US009492999B2

(12) United States Patent
Ward et al.

(10) Patent No.: US 9,492,999 B2
(45) Date of Patent: Nov. 15, 2016

(54) DROP DETECTION METHODS AND APPARATUS FOR USE WITH DROP DISPENSING APPARATUS

(71) Applicant: Hewlett-Packard Development Company, L.P., Houston, TX (US)

(72) Inventors: Kenneth Ward, Corvallis, OR (US); Alexander Govyadinov, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 14/588,821

(22) Filed: Jan. 2, 2015

(65) Prior Publication Data

US 2015/0116406 A1  Apr. 30, 2015

Related U.S. Application Data

(63) Continuation of application No. 13/123,804, filed as application No. PCT/US2008/011809 on Oct. 15, 2008, now Pat. No. 9,132,629.

(51) Int. Cl.
*B41J 2/045* (2006.01)
*G01N 35/10* (2006.01)
*B41J 2/21* (2006.01)

(52) U.S. Cl.
CPC .......... *B41J 2/04581* (2013.01); *B41J 2/0451* (2013.01); *B41J 2/0456* (2013.01); *B41J 2/0458* (2013.01); *B41J 2/04561* (2013.01); *B41J 2/2142* (2013.01); *G01N 35/1016* (2013.01); *G01N 2035/1034* (2013.01)

(58) Field of Classification Search
None
See application file for complete search history.

(56) References Cited

U.S. PATENT DOCUMENTS

| 4,779,003 | A  | 10/1988 | Tatsuno |
| 5,646,654 | A  | 7/1997  | Widder |
| 6,576,155 | B1 | 6/2003  | Barbera-Guillem |
| 6,744,046 | B2 | 6/2004  | Valaskovic et al. |
| 6,958,482 | B2 | 10/2005 | Martinez et al. |
| 7,483,767 | B2 | 1/2009  | Montaser et al. |

(Continued)

FOREIGN PATENT DOCUMENTS

| JP | 2004058627 A   | 2/2004 |
| KR | 20050092985 A  | 9/2005 |
| WO | 2010044765 A1  | 4/2010 |

OTHER PUBLICATIONS

International Searching Authority, "International Preliminary Report on Patentability", issued in connection with PCT Application No. PCT/US2008/011809, Apr. 19, 2011, 5 pages.

(Continued)

*Primary Examiner* — Bradley Thies
(74) *Attorney, Agent, or Firm* — HP Inc Patent Department

(57) ABSTRACT

Drop detection are disclosed. An example liquid dispensing device includes a controller to control dispensing of a first drop from a first orifice and a second drop from a second orifice, a sensor to monitor the first orifice to detect at least one of a presence or an absence of a drop from the first orifice and, in response to the sensor detecting an absence of the first drop, the controller is to classify the first orifice as at least one of occluded or non-functioning.

13 Claims, 1 Drawing Sheet

(56) References Cited

U.S. PATENT DOCUMENTS

| | | | |
|---|---|---|---|
| 7,909,424 B2* | 3/2011 | Giri et al. | 347/19 |
| 8,333,453 B2 | 12/2012 | Dudenhoefer et al. | |
| 2002/0140760 A1* | 10/2002 | Bruch et al. | 347/19 |
| 2002/0158938 A1* | 10/2002 | Doval | 347/22 |
| 2003/0090534 A1* | 5/2003 | Valero et al. | 347/19 |
| 2004/0233465 A1 | 11/2004 | Coyle et al. | |
| 2006/0044341 A1 | 3/2006 | Reichelsheimer et al. | |
| 2006/0172060 A1* | 8/2006 | Teichman et al. | 427/8 |
| 2006/0261295 A1 | 11/2006 | Barea | |
| 2007/0023037 A1 | 2/2007 | Larsen et al. | |
| 2007/0024658 A1 | 2/2007 | Diol et al. | |
| 2008/0018909 A1 | 1/2008 | Osaka et al. | |
| 2008/0186373 A1 | 8/2008 | Rolly | |
| 2008/0259107 A1* | 10/2008 | Farr et al. | 347/14 |
| 2009/0015609 A1* | 1/2009 | Choo | 347/9 |
| 2009/0086190 A1* | 4/2009 | Kodama et al. | 356/28 |
| 2009/0231403 A1 | 9/2009 | Shi et al. | |
| 2009/0244163 A1 | 10/2009 | Govyadinov | |
| 2009/0288580 A1 | 11/2009 | Cai | |
| 2010/0033519 A1 | 2/2010 | Cai et al. | |
| 2011/0109679 A1* | 5/2011 | Govyadinov et al. | 347/14 |
| 2011/0121021 A1 | 5/2011 | Dudenhoefer et al. | |
| 2011/0221815 A1 | 9/2011 | Ward et al. | |
| 2014/0098156 A1 | 4/2014 | Taff et al. | |

OTHER PUBLICATIONS

International Searching Authority, "International Search Report", issued in connection with PCT Application No. PCT/US2008/011809, mailed on May 29, 2009, 2 pages.

International Searching Authority, "Written Opinion", issued in connection with PCT Application No. PCT/ US2008/011809, mailed on May 29, 2009, 4 pages.

United States Patent and Trademark Office, "Notice of Allowance", issued in connection with U.S. Appl. No. 13/123,804, mailed on Nov. 5, 2014, 14 pages.

United States Patent and Trademark Office, "Final Office Action", issued in connection with U.S. Appl. No. 13/123,804, mailed on Jul. 18, 2014, 13 pages.

United States Patent and Trademark Office, "Office Action", issued in connection with U.S. Appl. No. 13/123,804, mailed on Mar. 31, 2014, 16 pages.

United States Patent and Trademark Office, "Final Office Action", issued in connection with U.S. Appl. No. 13/123,804, mailed on Sep. 19, 2013, 21 pages.

United States Patent and Trademark Office, "Office Action", issued in connection with U.S. Appl. No. 13/123,804, mailed on May 9, 2013, 15 pages.

United States Patent and Trademark Office, "Advisory Action", issued in connection with U.S. Appl. No. 13/123,804, mailed on Nov. 29, 2013, 3 pages.

United States Patent and Trademark Office, "Final Office Action", issued in connection with U.S. Appl. No. 14/123,194, mailed on Dec. 16, 2014, 20 pages.

United States Patent and Trademark Office, "Office Action", issued in connection with U.S. Appl. No. 14/123,194, mailed on Jun. 20, 2014, 15 pages.

International Searching Authority, "International Preliminary Report on Patentability", issued in connection with PCT Application No. PCT/US2011/038608, Dec. 2, 2013, 5 pages.

International Searching Authority, "International Search Report and Written Opinion", issued in connection with PCT Application No. PCT/US2011/038608, mailed on Feb. 17, 2012, 7 pages.

Particle Sciences, Inc., "Manufacture of Microspheres as Carrier Particles for Active Biomolecules", Technical Paper, accessed on Feb. 10, 2015 [http://www.particlesciences.com/docs/Manufacture_of_Microspheres_as_Carrier_Particles_for_Active_Biomolecules.pdf], 3 pages.

United States Patent and Trademark Office, "Notice of Allowance," issued in connection with U.S. Appl. No. 13/123,804, mailed on Jun. 9, 2015, 18 pages.

United States Patent and Trademark Office, "Notice of Allowance," issued in connection with U.S. Appl. No. 14/123,194, mailed on May 11, 2015, 27 pages.

United States Patent and Trademark Office, "Notice of Allowance," issued in connection with U.S. Appl. No. 13/123,804, mailed on Mar. 17, 2015, 21 pages.

United States Patent and Trademark Office, "Notice of Allowability," issued in connection with U.S. Appl. No. 13/123,804, mailed on Aug. 21, 2015, 4 pages.

United States Patent and Trademark Office, "Notice of Allowability," issued in connection with U.S. Appl. No. 14/123,194, mailed on Jul. 21, 2015, 4 pages.

* cited by examiner

Fig. 2 FOR A TOTAL INTENDED VOLUME OF 1000pL

| DROP VOLUME (pL) | 18 | 21 | 25 | 29 |
|---|---|---|---|---|
| TOTAL NUMBER DROPS | 56 | 48 | 40 | 34 |

DROP DETECTION METHODS AND APPARATUS FOR USE WITH DROP DISPENSING APPARATUS

RELATED APPLICATION

This patent arises from a continuation of U.S. patent application Ser. No. 13/123,804, which was filed on Apr. 12, 2011, which claims priority to International Patent Application Ser. No. PCT/US08/11809, filed Oct. 15, 2008, both of which are hereby incorporated herein by reference in their entireties.

BACKGROUND

Liquid dispensing devices, such as thermal ink jet printers, may be utilized to dispense precise and minute amounts of liquid, such as droplets of liquid, into individual wells of a multiple-well tray, such as in pharmaceutical testing, for example. Precise numbers of drops should be dispensed into the individual wells in order to ensure accurate test results. There is a need, therefore, to detect the number of drops dispensed from a liquid dispensing device. Moreover, there is a need for detecting the presence of drops from a liquid dispensing device to determine if the orifices of the device are functioning.

BRIEF DESCRIPTION OF THE DRAWINGS

FIG. 2 is a table showing a correlation between the intended total volume and the total number of drops to achieve the intended total volume for a particular drop volume.

DETAILED DESCRIPTION

Figure 1:
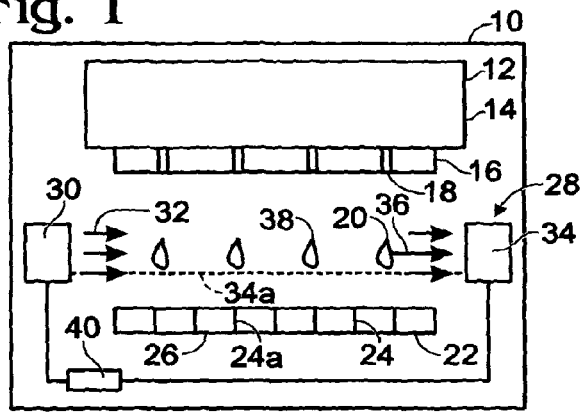
FIG. 1 is a schematic side cross-sectional view of one example embodiment of a liquid dispensing device.

FIG. 1 is a schematic side cross-sectional view of one example embodiment of a liquid dispensing device 10, which in the embodiment shown may include a drop ejection device 12. Drop ejection device 12 may be a printing or an imaging device, and in the example embodiment shown, may be a thermal ink jet device. Drop ejection device 12 may include a printhead or multiple printheads 14 that may each include an orifice layer 16, such as an orifice plate, for example, including multiple orifices 18 therein for ejecting fluid 20 therefrom. Drop ejection device 12 may be one of a thermal ejection device, and a piezo ejection device, for example.

Orifice layer 16 may include one or several orifices 18 or may include thousands of orifices 18, as may be suited for a particular application. Fluid 20 may be any fluid as desired for a particular liquid dispensing application. The drop ejection device 12 generates droplets 38 of fluid 20 of differing drop volumes depending on fluid 20 and construction details of device 12. In the field of pharmaceutical testing, fluid 20 may primarily be any water-miscible organic solvent, such as dimethyl sulfoxide (DMSO), for example. In other embodiments, fluid 20 may be primarily water, methanol, isopropanol, ethanol, glycerol, acetone, pyridine, tetrahydrofuran, acetonitrile, and dimethylformamide, for example.

Liquid dispensing device 10 may be utilized to dispense precise and minute amounts of liquid into a liquid receiving device 22, such as into individual wells 24 of a multiple-well tray 26, as used in pharmaceutical testing, for example. In some example embodiments liquid receiving device 22 may be a biochemical testing device, a diagnostic strip device, or a device to receive a coating, for example. Precise volume amounts should be dispensed into the individual wells 24 in order to ensure accurate test results. There is a need, therefore, to increase the reliability and/or predictability of the volume of fluid 20, such as the predictability of the number of drops 38, dispensed into each of the individual wells 24.

Liquid dispensing device 10 may include a drop detection device 28. The drop detection device may be chosen from one of an electrostatic detection device, a capacitive detection device, an acoustic drop detection device, and an optical detection device, for example. In the embodiment shown, drop detection device 28 may include a light emitting device 30 that emits a light 32, such as a laser, and a single light detecting device 34 positioned with respect to orifice layer 16 such that light detecting device 34 receives light 36 reflected, scattered or otherwise emanating from drops 38 of fluid 20 ejected from orifice 18 and illuminated by light 32. Light detecting device 34 may be a photodetector chosen from one of a photo diode, a CMOS, a charge-coupled device, a photo multiplying tube, and any other photodetector. Light emitting device 30 may be chosen from one of a laser, a light emitting diode, an arc discharge lamp, and any other high intensity light source.

Light detecting device 34 may be connected to a controller 40 that may use the light information received from light 36 by detecting device 34, so as to determine the number of drops ejected into, or to be ejected into, each compartment of liquid receiving device 22, such as into each of the individual wells 24 of a well tray 26, with each well 24 receiving different intended volumes, as one example.

Controller 40 may include a database of information such as electronically or otherwise stored formulas, graphs, tables, and the like that correlate different types of information, such as a correlation of drop volume for individual drops for a variety of fluid solutions, for example. Controller 40 may also include a means for determining the number of drops 38 of particular volume that are required for an intended dispense volume into an individual well 24. In the embodiment shown, drop detection device 28 is a light based detection device. However, drop detection device 28 may be an electrostatic device, a capacitive device, an acoustic device, a magnetic detection device, an optical device, or any other drop detection device that will function for a particular application.

In one example embodiment, drop detection device 28 may be a light scattering drop detector including a light emitting device 30, with a 1 millimeter) laser beam waist (the critical dimension in a drop's trajectory direction). Light detecting device 34 may be a single channel photocell or a photocell array that is capable of detecting up to 5,000 to 8,000 drop-events per second at a nominal drop velocity >10 m/s, which is typical for both thermal and piezo-ink jet technologies. Using a 0.1 mm laser beam waist, the same detector may be capable of detecting up to 50,000 to 80,000 drop-events per second at the same drop ejecting conditions. As the drops 38 fall, light 32 from laser diode 30 illuminates the drop 38, and light 36 scattered from the drops is detected by photo cell 34. At a drop velocity at 10 m/second, the expected time-of-flight (TOF) of the drops is 10 micro seconds (μsec). The single channel light detection device 34 may be positioned at a single, predetermined angle 34a relative to the direction of incident light 32 from laser diode 30. Accordingly, angle 34a is shown as the angle between incident light 32 and scattered light 36. In the embodiment shown in FIG. 1, angle 34a is near 0°, i.e., device 34 is positioned almost in line with the path of light 32 from light emitting device 30. At angle of 0° a shadow effect by obscuring light by the drop will occur. The device will detect scattering light from near 0° up to 180°, which corresponds to complete back scattering/retro reflection. For typical inkjet drop sizes >10 μm a diffraction is significant at low angles (close to 0°) and may have a significant contribution at higher angles only for small particles and long light wavelengths such as when the particle size is comparable and even smaller than the wavelength. In one preferred embodiment, an angle of 10-45° is utilized for light scattering. In general, angles of 10-90 degrees are readily useable, with large signals closer to 0 degrees, although there is a decrease of light intensity at exactly zero degrees because of superposition of the shadow effect and low angular diffraction contributions. Accordingly, an angle 34a of 20 degrees for particular implementation may be desirable.

In one embodiment the drops 38 may continue to fall into a drop collection reservoir (not shown) for later use in liquid dispensing device 10, such that the fluid is not wasted, or drops 38 may fall into a separate reservoir (not shown) to be collected for disposal. However, in the embodiment shown the drops 38 fall directly into a predetermined individual well, such as a well 24a, for example, of well tray 26 and real time processing is conducted to determine the exact number of drops to be dispensed into the particular well 24a so that well 24a will contain a minute, precise, predetermined and known volume of fluid 20.

In a simple embodiment, light emitting device 30 may be a laser diode or a light emitting diode (LED) and light detecting device 34 may be a single photodiode, which may be interfaced via a preamplifier to a pulse counter on a single personal computer or a controller device such as an FPGA or PLC for example. In more sophisticated implementations, a peak detector may be used to measure a value of the amplitude signal, which will be used for number of drops evaluation as well (see FIG. 3). This versatile system could be used to count drops that are being generated up to 100 KHz and accomplish the counting in real time, as opposed to offline precalibration methods such as optical or gravimetric methods currently utilized. Accordingly, the current device provides extremely rapid feedback to the dispense system. Moreover, because every drop is counted, the precision and accuracy of the disclosed method is better than gravimetric or optical methods currently in use. Furthermore, use of a single light detection device 34, positioned at a single angle 34a with respect to light emitting device 30, greatly simplifies the device operation and lowers the cost of device 1, and greatly simplifies the mathematical calculations that may be conducted by controller 40 in determining a drop count of drops 38 from printhead 14.

In another embodiment, drop detection device 28 may be utilized to determine a health of individual ones of orifices 18 of orifice layer 16. In particular, drop detection device 28 may be utilized to determine the presence or absence of a drop ejected from a particular orifice of multiple orifices 18. The absence of a drop ejected from a particular orifice when a drop is attempted to be ejected from that orifice, will be determined by the controller 40 to indicate that the particular orifice is occluded or otherwise is in a state of bad health. Conversely, the presence of a drop ejected from a particular orifice when a drop is attempted to be ejected from that orifice, may be determined by the controller 40 to indicate that the particular orifice is not occluded or otherwise is in a state of good health. If a particular orifice is determined to be occluded or otherwise in bad health, controller 40 may control ejection of fluid 20 from one or more healthy orifices to compensate for the occlusion of the particular orifice. If more than a specified threshold number of orifices 18 are determined to be in had health, controller 40 may notify the operator that drop ejection device 12 is not useful to dispense the required dispense volume and prompt the operator and use a different drop ejection device 12.

In another implementation the peak detector signal may be used to evaluate a real number of dispensed drops from simultaneously firing nozzles. The method enables high throughput and high precision.

FIG. 2 is a table 66 showing a correlation, at a particular total intended volume of 1,000 picoliters, between a particular drop volume 68, determined by or stored in controller 40, in picoliters of drops 38 from printhead 14, and the total number of drops 70 that should be ejected to ensure the intended total volume within an individual well 24a of wall tray 26. For example, a desired total intended volume in a well 24a of 1,000 picoliters is achieved by ejecting a total of forty drops 38 into well 24a from printhead 14 when the drop volume is 25 pL. The total of forty drops may be calculated to include drops that previously have been dispensed into well 24a, such as during a setup or calibration step such as orifice health determinations or drop volume determinations by controller 40. For this method, the drops ejected for the orifice health or drop volume determination would be counted as they are dispensed into a well 24a which is later intended to have a sufficiently large dispensed volume. The number of drops dispensed into this well during the orifice health or drop volume determination steps may be subtracted from the intended number of drops for well 24a to determine the correct number of drops remaining to be dispensed. After the correct number of drops required for each individual well 24a are determined, the dispensing into well tray 26 may proceed, including real time drop counting to dispense the exact number of drops required.

In this manner, a quick, efficient and accurate total number of drops 70 may be placed into multiple individual liquid receiving compartments 24 of a liquid receiving device on a large scale to achieve multiple intended total volumes. For example, minute and precise volumes of liquid 20 may be dispensed into the individual wells 24 of a well tray 26 that may include hundreds or thousands of individual wells 24, for example.

Advantages of the drop count determination of the process described herein include the lack of use of fluid additives to enable drop detection, improved accuracy and precision of dispensed volumes, the speed of the drop volume calculation method, and the lack of use of expensive detection hardware. Moreover, this method may be used "on-line" or in "real-time" during filling of a well tray, or before filling a well tray during a set-up or calibration routine.

The information contained in FIG. 2 is a very small sample shown for ease of illustration. In practice, much more information may be contained within the database or databases of controller 40 to allow the precise calculation of desired dispense volumes.

Figure 3:
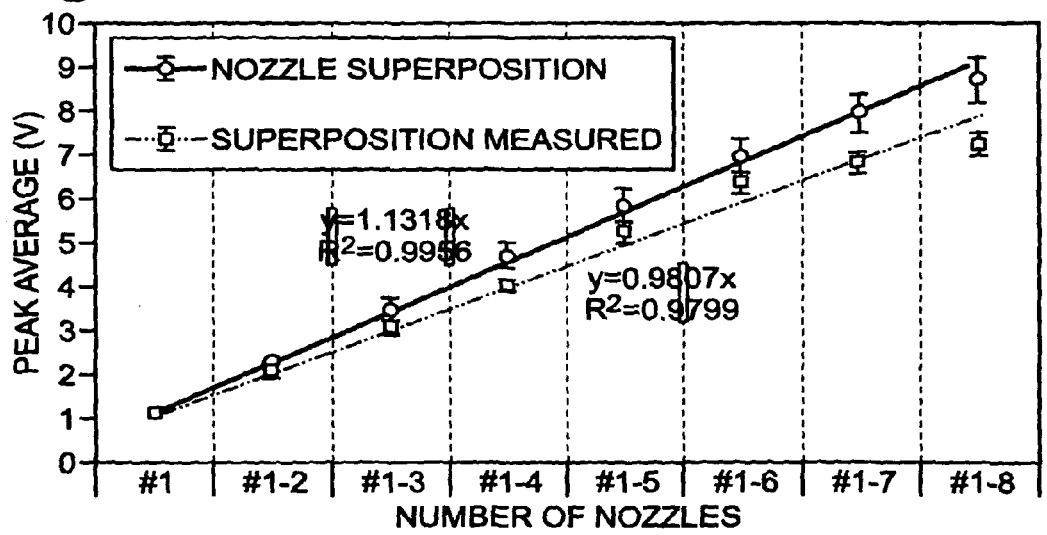
FIG. 3 is an exemplary plot showing dependency of signal strength versus number of simultaneously exposed drops.

FIG. 3 shows an exemplary plot showing dependency of signal strength versus number of simultaneously exposed drops.

An example liquid dispensing device (10) disclosed herein includes a drop ejection device (12) including an orifice (18) adapted for ejecting drops therefrom, a single detection device (28) positioned to receive drop information from the ejected drops of the drop ejection device, and a controller (40) that receives the drop information and uses the drop information to determine a number of drops ejected from the drop ejection device. In some examples, the drop ejection device (12) is one of a thermal ejection device, and a piezo ejection device and the single detection device (28) is one of an electrostatic detection device, a capacitive detection device, an acoustic drop detection device, and an optical detection device.

In some examples, the single detection device including a light scattering drop detection device including a light source such as a laser, a light emitting diode, or an arc discharge lamp. In some examples, the detection device also includes a photodetector chosen such as a photo diode, a CMOS, a charge-coupled device, or a photo multiplying tube. In some examples, the controller (40) uses the light scattering information to determine a health of individual orifices of the drop ejection device.

An example method of dispensing liquid disclosed herein includes ejecting drops (20) from at least one orifice (18), counting a number of the ejected drops using a single detection device, and calculating a dispensed volume of the ejected drops from the counted number of drops. In some examples, the method also includes ejecting drops from multiple orifices (18) simultaneously. In some examples, the calculating includes correlating the counted number of drops with a drop volume of each drop to determine the dispensed volume. In some examples, counting the number of ejected drops is conducted utilizing electrostatic detection, capacitive detection, acoustic drop detection, or optical detection. In some examples, counting the number of ejected drops is conducted with a light scattering drop detection device (28) including a light source such as a laser, a light emitting diode, or an arc discharge lamp. Sin some examples, the counting is performed using a photodetector such as a photo diode, a CMOS, a charge-coupled device, or a photo multiplying tube. In some examples, the calculating a dispensed volume is conducted during real time filling of a multiple-well liquid receptacle (26), and drops ejected during the counting are subtracted from the total dispense volume required for each wells. In some examples, the counting is conducted prior to real time filling of a receptacle. In some examples, the method includes positioning a liquid receiving device to receive an intended volume of the ejected drops. In some examples, the liquid receiving device is a biochemical testing device or a diagnostic strip device. In some examples, the drops exhibit an absence of a light detection reagent added to the drops.

Other variations and modifications of the concepts described herein may be utilized and fall within the scope of the claims below.

What is claimed is:

1. A liquid dispensing device, comprising:
    a controller to control dispensing of a first drop from a first orifice and a second drop from a second orifice;
    a sensor to monitor the first orifice to detect at least one of a presence or an absence of a drop from the first orifice and to monitor the second orifice to detect at least one of a presence or an absence of a drop from the second orifice;
    in response to the sensor detecting an absence of the first drop, the controller to classify the first orifice as at least one of occluded or non-functioning;
    in response to the sensor detecting a presence of the second drop, the controller to classify the second orifice as functional;
    when the first orifice is classified as at least one of occluded or non-functioning, the second orifice is classified as functional, and the first orifice was dispensing a first fluid solution prior to being classified as the at least one of occluded or non-functioning, the controller to cause the second orifice to dispense drops of the first fluid solution toward a drop receiving well until a tally of drops received within the drop receiving well satisfies a first threshold; and
    when the first orifice is classified as the at least one of occluded or non-functioning, the second orifice is classified as functional, and the first orifice was dispensing a second fluid solution prior to being classified as the at least one of occluded or non-functioning, the controller to cause the second orifice to dispense drops of the second fluid solution toward the drop receiving well until a tally of drops received within the drop receiving well satisfies a second threshold, the first fluid solution being different from the second fluid solution, the first threshold being different from the second threshold.

2. The liquid dispensing device of claim 1, wherein the sensor includes a light scattering drop detector.

3. The liquid dispensing device of claim 1, wherein the sensor includes a photocell or a photocell array.

4. The liquid dispensing device of claim 1, wherein, when the second orifice is classified as at least one of occluded or non-functioning, the first orifice is classified as functional, and the second orifice was dispensing a third fluid solution prior to being classified as the at least one of occluded or non-functioning, the controller to cause the first orifice to dispense drops of the third fluid solution toward the drop receiving well until a tally of drops received within the drop receiving well satisfies a third threshold; and
    when the second orifice is classified as at least one of occluded or non-functioning, the first orifice is classified as functional, and the second orifice was dispensing a fourth fluid solution prior to being classified as the at least one of occluded or non-functioning, the controller to cause the first orifice to dispense drops of the fourth fluid solution toward the drop receiving well until a tally of drops received within the drop receiving well satisfies a fourth threshold, the third fluid solution being different from the fourth fluid solution, the third threshold being different from the fourth threshold.

5. The liquid dispensing device of claim 4, wherein the first fluid solution is different from the third fluid solution, the first fluid solution is different from the fourth fluid solution, the first threshold is different from the third threshold, the first threshold is different from the fourth threshold.

6. The liquid dispensing device of claim 1, wherein, when the second orifice is classified as at least one of occluded or non-functioning, the first orifice is classified as functional, and the second orifice was dispensing a first fluid solution prior to being classified as the at least one of occluded or non-functioning, the controller to cause the first orifice to dispense drops of the first fluid solution toward the drop receiving well until a tally of drops received within the drop receiving well satisfies the first threshold; and
    when the second orifice is classified as at least one of occluded or non-functioning, the first orifice is classified as functional, and the second orifice was dispensing a second fluid solution prior to being classified as the at least one of occluded or non-functioning, the controller to cause the first orifice to dispense drops of the second fluid solution toward the drop receiving well until a tally of drops received within the drop receiving well satisfies the second threshold.

7. The liquid dispensing device of claim 1, wherein the sensor is to detect the drops dispensed from the second orifice as the drops descend toward the drop receiving well.

8. The liquid dispensing device of claim 1, wherein the sensor is a first sensor, and further including a second sensor to monitor the first orifice to detect at least one of a presence or an absence of a drop from the first orifice and to monitor the second orifice to detect at least one of a presence or an absence of a drop from the second orifice.

9. The liquid dispensing device of claim 1, wherein the controller is coupled to a database that stores associations between fluid solutions and respective drop volumes including a first association between the first fluid solution and a first drop volume and a second association between the second fluid solution and a second drop volume, the controller to use the first association to determine the first threshold of drops of the first fluid solution that satisfies a first volume in the drop receiving well, the controller to use the second association to determine the second threshold of drops of the second fluid solution that satisfies a second volume in the drop receiving well, the first and second volumes being the same.

10. A method, comprising:
   initiating dispensing a first drop from a first orifice and a second drop from a second orifice;
   monitoring the first orifice, via a sensor, to detect at least one of a presence or an absence of a drop from the first orifice;
   monitoring the second orifice to detect at least one of a presence or an absence of a drop from the second orifice;
   in response to detecting an absence of the first drop, classifying the first orifice as occluded or otherwise non-functional;
   in response to detecting a presence of the second drop, classifying the second orifice as functional;
   when the first orifice is classified as at least one of occluded or non-functioning, the second orifice is classified as functional, and the first orifice was dispensing a first fluid solution prior to being classified as the at least one of occluded or non-functioning, causing the second orifice to dispense drops of the first fluid solution toward a drop receiving well until a tally of drops received within the drop receiving well satisfies a first threshold; and
   when the first orifice is classified as at least one of occluded or non-functioning, the second orifice is classified as functional, and the first orifice was dispensing a second fluid solution prior to being classified as the at least one of occluded or non-functioning, causing the second orifice to dispense drops of the second fluid solution toward the drop receiving well until a tally of drops received within the drop receiving well satisfies a second threshold, the first fluid solution being different from the second fluid solution, the first threshold being different from the second threshold.

11. The method of claim 10, further including providing a notification when a threshold number of the orifices become occluded or otherwise nonfunctional.

12. The method of claim 10, further including, when the first orifice is classified as at least one of occluded or non-functioning the second orifice is classified as functional, and the first orifice was dispensing a third fluid solution prior to being classified as the at least one of occluded or non-functioning, causing the second orifice to dispense drops of the third fluid solution toward the drop receiving well until a tally of drops received within the drop receiving well satisfies a third threshold; and
   when the first orifice is classified as at least one of occluded or non-functioning, the second orifice is classified as functional, and the first orifice was dispensing a fourth fluid solution prior to being classified as the at least one of occluded or non-functioning, causing the second orifice to dispense drops of the fourth fluid solution toward the drop receiving well until a tally of drops received within the drop receiving well satisfies a fourth threshold, the third fluid solution being different from the fourth fluid solution, the third threshold being different from the fourth threshold.

13. The method of claim 12, wherein the first fluid solution is different from the third fluid solution, the first fluid solution is different from the fourth fluid solution, the first threshold is different from the third threshold, the first threshold is different from the fourth threshold.

* * * * *